United States Patent
Kim et al.

(10) Patent No.: US 9,512,418 B2
(45) Date of Patent: Dec. 6, 2016

(54) METHOD FOR PRODUCTION OF BOTULINUM TOXIN

(71) Applicant: DAEWOONG Co., LTD., Seongnam-si, Gyeonggi-do (KR)

(72) Inventors: Chung Sei Kim, Seoul (KR); Kwan Young Song, Bucheon-si (KR); Kyoung Min Min, Chuncheon-si (KR); Yeong Duk An, Daegu (KR)

(73) Assignee: Daewoong Co., Ltd., Seongnam-si, Gyeonggi-do (KR)

(*) Notice: Subject to any disclaimer, the term of this patent is extended or adjusted under 35 U.S.C. 154(b) by 0 days.

(21) Appl. No.: 14/654,819

(22) PCT Filed: May 7, 2014

(86) PCT No.: PCT/KR2014/004003
§ 371 (c)(1),
(2) Date: Jun. 22, 2015

(87) PCT Pub. No.: WO2015/016462
PCT Pub. Date: Feb. 5, 2015

(65) Prior Publication Data
US 2015/0337281 A1    Nov. 26, 2015

(30) Foreign Application Priority Data
Aug. 2, 2013   (KR) .................. 10-2013-0092024

(51) Int. Cl.
C07K 14/33      (2006.01)
C12N 9/52       (2006.01)

(52) U.S. Cl.
CPC .............. C12N 9/52 (2013.01); C07K 14/33 (2013.01); *C12Y 304/24069* (2013.01)

(58) Field of Classification Search
CPC ................. C07K 14/33; C12Y 304/24069
See application file for complete search history.

(56) References Cited

U.S. PATENT DOCUMENTS

| | | | |
|---|---|---|---|
| 7,452,697 B2 | 11/2008 | Luo et al. | |
| 2005/0238669 A1 | 10/2005 | Xiang et al. | |
| 2006/0228780 A1 | 10/2006 | Luo et al. | |
| 2011/0008843 A1 | 1/2011 | Ton et al. | |

FOREIGN PATENT DOCUMENTS

| | | |
|---|---|---|
| KR | 10-2003-0060150 A | 7/2003 |
| KR | 10-2009-0091501 A | 8/2009 |
| KR | 10-2011-0091492 A | 8/2011 |
| WO | 2011-050072 A1 | 4/2011 |
| WO | WO 2011050072 A1 * | 4/2011 ............ C12N 9/52 |

OTHER PUBLICATIONS

Jung et al. 2003; KR20030060150; machine translation.*
International Search Report dated Aug. 27, 2014 of PCT/KR2014/004003 which is the parent application—3 pages.
Schantz et al., "Properties and Use of Botulinum Toxin and Other Microbial Neurotoxins in Medicine", Microbiological Reviews, Mar. 1992, vol. 56, No. 1, pp. 80-99.
Sugiyama, "Clostridium botulinum Neurotoxin", Microbiological Reviews, Sep. 1980, vol. 44, No. 3, pp. 419-448.
Park et al., "Binding of Clostridium botulinum type B toxin to rat brain synaptosome", FEMS Microbiology Letters, 1990, vol. 72, pp. 243-248.
Poulain et al., "Neurotransmitter release is blocked intracellularly by botulinum neurotoxin, and this requires uptake of both toxin polypeptides by a process mediated by the larger chain", Proc. Natl. Acad. Sci. USA, Jun. 1988, vol. 85, pp. 4090-4094.
Simpson, "Molecular pharmacology of Botulinum Toxin and Tetanus Toxin", Ann. Rev. Pharmacol. Toxicol., 1986, vol. 26, pp. 427-453.
Binz et al., "The Complete Sequence of Botulinum Neurotoxin Type A and Comparison with Other Clostridial Neurotoxins", The Journal of Biological Chemistry, 1990, vol. 265, No. 16, pp. 9153-9158.
Simpson et al., "Isolation and Characterization of the Botulinum Neurotoxins", Methods in Enzymology, 1988 vol. 165, pp. 76-85.
Montecucco et al., "Tetanus and botulism neurotoxins: a new group of zinc proteases", Trends in Biochemical Sciences, 1993, vol. 18, pp. 324-327.
Extended European search report for European application No. 14 83 2966, six pages, completed Jul. 6, 2016.

* cited by examiner

*Primary Examiner* — Karen Cochrane Carlson
(74) *Attorney, Agent, or Firm* — Vorys, Sater, Seymour & Pease LLP; Mih Suhn Koh

(57) ABSTRACT

A method of making botulinum toxin comprises treating a culture of a botulinum toxin-producing strain with acid to precipitate a botulinum toxin; adding buffer to the precipitated botulinum toxin, followed by treatment with a protease inhibitor and nuclease, thereby extracting the botulinum toxin; treating the extracted botulinum toxin with acid to precipitate the botulinum toxin and dissolving the precipitate in buffer; and purifying the botulinum toxin by anion exchange chromatography. The use of the method makes it possible to produce a high-purity botulinum toxin by a simple process. The botulinum toxin produced by the method has high purity, and thus has an increased ability to act in a local area. Thus, the systemic circulation of the botulinum toxin is reduced to increase the safety. Accordingly, the botulinum toxin can be used for treatment of neuromuscular disorders, removal of wrinkles, and treatment of spastic hemiplegia and cerebral palsy.

13 Claims, 3 Drawing Sheets

US 9,512,418 B2

METHOD FOR PRODUCTION OF BOTULINUM TOXIN

TECHNICAL FIELD

The present invention relates to a method for production of a botulinum toxin, and more particularly to a method for preparation of botulinum toxin, the method comprising the steps of: (a) treating a culture of a botulinum toxin-producing strain with acid to precipitate a botulinum toxin; (b) adding buffer to the precipitated botulinum toxin, followed by treatment with a protease inhibitor and nuclease, thereby extracting the botulinum toxin; (c) treating the extracted botulinum toxin with acid to precipitate the botulinum toxin and dissolving the precipitate in buffer; and (d) purifying the botulinum toxin by anion exchange chromatography.

BACKGROUND ART

A variety of *Clostridium* sp. strains that secrete neurotoxins have been discovered since 1890s, and the characterization of toxins that are secreted from these strains has been made for the past 70 years (Schant, E. J. et al., *Microbiol. Rev.*, 56:80, 1992).

Neurotoxins derived from the *Clostridium* sp. strains, that is, botulinum toxins, are classified into seven types (types A to G) depending on their serological properties. Each of the toxins has a toxin protein having a size of about 150 KDa and naturally contains a complex of several non-toxic proteins. A medium complex (300 kDa) is composed of a toxin protein and a non-toxic non-hemagglutinin protein, and a large complex (450 kDa) and a very large complex (900 kDa) are composed of the medium complex bound to hemagglutinin (Sugiyama, H., *Microbiol. Rev.*, 44: 419, 1980). Such non-toxic hemagglutinin proteins are known to function to protect the toxin from low pH and various proteases in the intestines.

The toxin is synthesized as a single polypeptide having a molecular weight of about 150 kDa in cells, and then cleaved at a position of ⅓ starting from the N-terminal end by the action of intracellular protease or treatment with an artificial enzyme such as trypsin into two units: a light chain (L; molecular weight: 50 kDa) and a heavy chain (H; molecular weight: 100 kDa). The cleaved toxin has greatly increased toxicity compared to the single polypeptide. The two units are linked to each other by a disulfide bond and have different functions. The heavy chain binds to a receptor of a target cell (Park. M. K., et al., *FEMS Microbiol. Lett.*, 72:243, 1990) and functions to interact with a biomembrane at low pH (pH 4) to form a channel (Mantecucco, C. et al., *TIBS.*, 18:324, 1993), and the light chain has pharmacological activity, and thus imparts permeability to cells using a detergent or interferes with the secretion of a neurotransmitter when introduced into cells by, for example, electroporation (Poulain, B. et al., *Proc. Natl. Acad. Sci. USA.*, 85:4090, 1988).

The toxin inhibits the exocytosis of acetylcholine at the cholinergic presynapse of a neuromuscular junction to cause asthenia. It has been considered that treatment with a very small amount of the toxin exhibits toxicity, suggesting that the toxin has any enzymatic activity (Simpson, L. L. et al., *Ann. Rev. Pharmaeol. Toxicol.*, 26:427, 1986).

According to a recent report, the toxin has metallopeptidase activity, and its substrate is composed of synaptobrevin, syntaxin, a synaptosomal associated protein of 25 KDa (SNAP25) or the like, which are the unit proteins of an exocytosis machinery complex. Each type of toxin uses one of the above-described three proteins as its substrate, and it is known that type B, D, F and G toxins cleave synaptobrevin at a specific site, type A and E toxins cleave SNAP25 at a specific site, and type C cleaves syntaxin at a specific site (Binz, T. et al., *J. Biol. Chem.*, 265:9153, 1994).

Particularly, type A botulinum toxin is known to be soluble in a dilute aqueous solution at a pH of 4.0-6.8. It is known that a stable non-toxic protein is separated from neurotoxin at a pH of about 7 or higher, and as a result, the toxicity is gradually lost. Particularly, it is known that the toxicity decreases as pH and temperature increase.

The botulinum toxin is fatal to the human body even in small amounts and is easy to produce in large amounts. Thus, it constitutes four major bio-terror weapons together with *Bacillus anthracis, Yersinia pestis* and smallpox virus. However, it was found that, when type A botulinum toxin is injected at a dose that does not systematically affect the human body, it can paralyze local muscle in the injected site. Based on this characteristic, type A botulinum toxin can be used in a wide range of applications, including wrinkle removing agents, agents for treating spastic hemiplegia and cerebral palsy, etc. Thus, the demand for type A botulinum toxin has increased, and studies on methods of producing botulinum toxin so as to satisfy the demand have been actively conducted.

A current typical commercial product is BOTOX® (a purified neurotoxin complex of type A botulinum toxin) that is commercially available from Allergan, Inc., USA. A 100-unit vial of BOTOX® is composed of about 5 ng of a purified neurotoxin complex of type A botulinum toxin, 0.5 mg of human serum albumin and 0.9 mg of sodium chloride and is reconstituted using sterile saline without a preservative (injection of 0.9% sodium chloride). Other commercial products include Dysport® (a complex of *Clostridium botulinum* type A toxin and hemagglutinin, which has lactose and human serum albumin in a pharmaceutical composition containing botulinum toxin and is reconstituted using 0.9% sodium chloride before use) that is commercially available from Ipsen Ltd., UK, MyoBloc™ (an injectable solution (a pH of about 5.6) comprising botulinum type B toxin, human serum albumin, sodium succinate and sodium chloride) that is commercially available from Solstice Neurosciences, Inc. Conventional methods used to produce botulinum toxins include an acid precipitation method, a precipitation method by salt, and a chromatographic method.

For example, Japanese Patent Laid-Open Publication No. 1994-192296 discloses a method of producing a crystalline botulinum type A toxin by culturing *Clostridium botulinum* bacteria, followed by acid precipitation, extraction, addition of nuclease, and crystallization. Further, U.S. Pat. No. 5,696,077 discloses a method of a crystalline botulinum type B toxin by culturing *Clostridium botulinum* bacteria, followed by acid precipitation, extraction, ion exchange chromatography, gel filtration chromatography and crystallization.

Simpson et al. produced a botulinum type A toxin by purifying botulinum neurotoxin by gravity flow chromatography, followed by HPLC, capture using affinity resin, size exclusion chromatography, and ion (anion and cation) exchange chromatography including the use of two different ion exchange columns (*Method in Enzymology*, 165:76, 1988), and Wang et al. used precipitation and ion chromatography to purify a botulinum type A toxin (*Dermatol Las Faci Cosm Surg.*, 2002:58, 2002).

Moreover, U.S. Pat. No. 6,818,409 discloses the use of ion exchange and lactose columns to purify a botulinum toxin, and U.S. Pat. No. 7,452,697 discloses a botulinum type A toxin by ion exchange chromatography and hydrophobic chromatography. Korean Patent Laid-Open Publication No. 2009-0091501 discloses a method of purifying a botulinum toxin by acid precipitation and anion exchange chromatography, and US Publication No. 2013-0156756 discloses a method of purifying a botulinum toxin by anion exchange chromatography and cation exchange chromatography.

However, the conventional methods have problems in that the use of anion exchange chromatography adversely affects the gel banding pattern of botulinum toxins (U.S. Pat. No. 7,452,697) and in that these conventional methods are difficult to apply commercially, due to a long purification time. In addition, because *Clostridium botulinum* that is a botulinum toxin-producing strain is an anaerobic bacterium, there is a problem in that fermentation of the bacterium should be performed in an anaerobic system, and thus it is difficult to produce botulinum toxins in large amounts. In addition, there is a problem in that the active ingredient botulinum toxin purified by the above-described purification method is not clearly separated and identified, and thus contains impurities. Additionally, the conventional methods for production of botulinum toxins have a problem in that a filtration or dialysis process is necessarily performed to purify a high-purity botulinum toxin, suggesting that the purification process is complex and difficult.

Accordingly, the present inventors have made extensive efforts to solve the above-described problems occurring in the prior art, and as a result, have found that when a culture of a botulinum toxin-producing strain is treated with acid to form a botulinum toxin precipitate and the formed precipitate is purified by anion exchange chromatography, the steps of filtration, dialysis and ethanol precipitation can be omitted, and the process for production of the botulinum toxin is very easy, and a botulinum toxin having a purity of 98% or higher can be produced by this production method, thereby completing the present invention.

SUMMARY OF INVENTION

It is an object of the present invention to provide a method of producing a high-purity botulinum toxin by a simple process.

To achieve the above object, the present invention provides a method for production of botulinum toxin, the method comprising the steps of: (a) treating a culture of a botulinum toxin-producing strain with acid to precipitate a botulinum toxin; (b) adding buffer to the precipitated botulinum toxin, followed by treatment with a protease inhibitor and nuclease, thereby extracting the botulinum toxin; (c) treating the extracted botulinum toxin with acid to precipitate the botulinum toxin and dissolving the precipitate in buffer; and (d) purifying the botulinum toxin by anion exchange chromatography.

DETAILED DESCRIPTION OF INVENTION AND PREFERRED EMBODIMENTS

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

Figure 1:
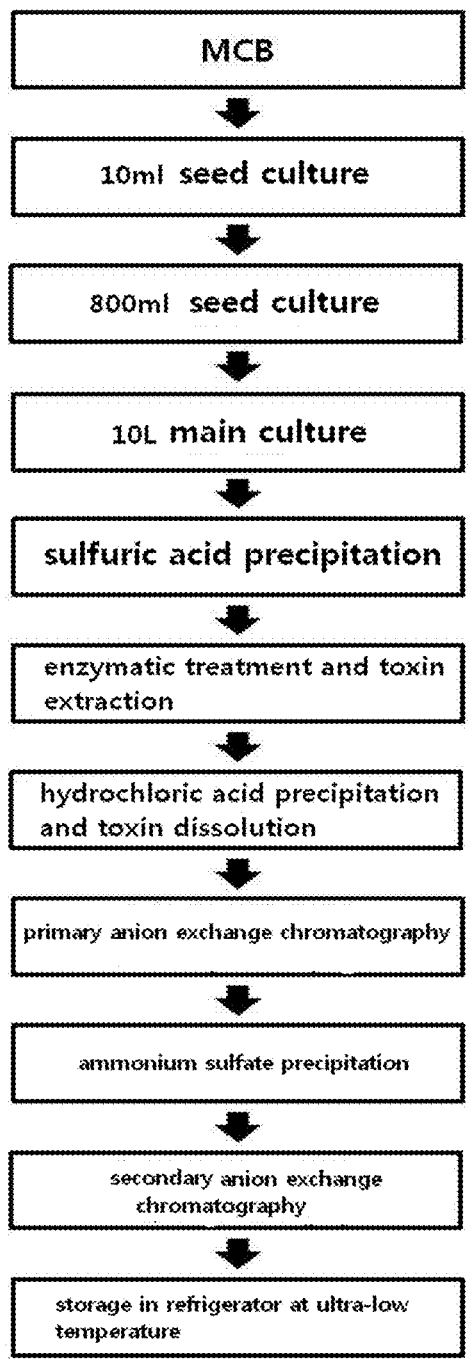
FIG. 1 is a schematic view showing a process of producing a botulinum toxin according to the present invention.

In one aspect, the present invention is directed to a method for production of botulinum toxin, the method comprising the steps of: (a) treating a culture of a botulinum toxin-producing strain with acid to precipitate a botulinum toxin; (b) adding buffer to the precipitated botulinum toxin, followed by treatment with a protease inhibitor and nuclease, thereby extracting the botulinum toxin; (c) treating the extracted botulinum toxin with acid to precipitate the botulinum toxin and dissolving the precipitate in buffer; and (d) purifying the botulinum toxin by anion exchange chromatography (FIG. 1).

The resulting botulinum toxin produced by the method of the present invention can be stored by various methods, including frozen storage and lyophilized storage.

The method of the present invention may further comprise, after step (d), the steps of: (e) treating an anion exchange chromatography fraction containing the botulinum toxin with ammonium sulfate to form a precipitate, and dissolving the precipitate in buffer; and (f) purifying the botulinum toxin by anion exchange chromatography.

In the present invention, the botulinum toxin-producing strain is preferably *Clostridium botulinum*, but is not limited thereto, and it will be apparent to those skilled in the art that any strain capable of producing a botulinum toxin may be used in the present invention.

As used herein, the term "botulinum toxin" is means to include not only a neurotoxin produced by the *Clostridium botulinum* strain, but also modified, recombinant, hybrid and chimeric botulinum toxins. A recombinant botulinum toxin may have a light chain and/or heavy chain produced by non-*Clostridium* species in a recombinant manner. In addition, the term "botulinum toxin" as used herein is meant to include botulinum toxin serotypes A, B, C, D, E, F and G, botulinum toxin complexes (i.e., 300, 600 and 900 kDa complexes), and a pure botulinum toxin (i.e., 150 kDa neurotoxic molecule), which are all useful in the practice of the present invention.

As used herein, the term "produced botulinum toxin" means a pure botulinum toxin or a botulinum toxin complex, which is separated or substantially separated from other proteins or impurities that can be accompanied by the botulinum toxin when the botulinum toxin is collected from a culture or fermentation process. Thus, the produced botulinum toxin has a purity of at least 90%, preferably at least 95%, and most preferably at least 98%. Particularly, the produced botulinum toxin in the present invention may be a botulinum type A toxin protein having a purity of at least 98%.

Culture of the *Clostridium botulinum* strain for producing the botulinum toxin can be performed using a conventional method known in the art and a conventional medium that may be used for culture.

By way of non-limiting example, a medium for culture of *Clostridium botulinum* strain may include a casein hydrolysate, a yeast extract, glucose and the like, and the culture is performed at a temperature of 25 to 40° C. for 90-180 hours, and preferably 100-150 hours.

The acid precipitation of step (a) may be performed by adding acid, preferably sulfuric acid or hydrochloric acid, to a culture of the strain, so that the culture reaches a pH of 3.0-4.5, preferably 3.3-4.0, and most preferably 3.4-3.6, as measured by a pH sensor.

The acid precipitation of step (a) is based on the principle in which the addition of acid to a culture containing many kinds of proteins reduces the pH of the culture while killing botulinum bacteria remaining after culture so that the proteins reach the isoelectric point to precipitate. It includes crystallization in a broad sense, and the precipitation method is a method of roughly separating a desired material in a mixed state, unlike crystallization focused on purifying the desired material with high purity. In the precipitation method, impurities having a structure similar to the desired material are also precipitated. Herein, the pH is adjusted to about 3.0-4.5. The recovery rate of the botulinum toxin increases as the pH decreases. If the pH is 3.0 or lower, it will affect the botulinum toxin itself, and if the pH is 4.5 or higher, the recovery rate of the botulinum toxin will decrease. For these reasons, the pH is preferably within the above-specific range.

Particularly, the pH is most preferably 3.4-3.6, because the recovery rate of the botulinum toxin is the highest in this pH range. When the pH of the botulinum strain culture reaches a suitable range after addition of acid, the acid is added to the culture until the change in the pH no longer appears, and then the culture is allowed to stand at room temperature for 15-30 hours, followed by removal of the supernatant.

Step (b) of extracting the botulinum toxin comprises a step of dissolving the toxin resulting from step (a) in phosphate buffer, preferably sodium phosphate buffer, and removing the precipitate. Herein, the pH of the phosphate buffer is preferably about 4.0 to about 7.0. The resulting pH can be adjusted to 4.5-6.5, preferably 5.0-6.0, by addition of a base, preferably sodium hydroxide, and extraction of the toxin can be performed in the above-specified pH range.

In addition, nuclease that is used in step (b) may be DNase and RNase, and the protease inhibitor that is used in step (b) is preferably benzamidine HCl, but is not limited thereto, and any material capable of inhibiting protease activity, known in the art, may be used in the present invention. By treatment with nuclease in step (b) of extracting the botulinum toxin, impurities such as DNA and RNA contained in the precipitate formed by acid in step (a) can be degraded. If the step of treatment with the enzyme is carried out for 1.5 hours or less, degradation of DNA and RNA can be insufficient. For this reason, the step of treatment with the enzyme is carried out for 1.5-7 hours, preferably 3-6 hours, and DNase and RNase are preferably added at a concentration of 0.05-1.0 g/l, preferably 0.1-0.5 g/l.

Because the extract obtained by the enzymatic treatment contains the botulinum toxin and a protein having polarity similar to that of the botulinum toxin, a step of precipitating the protein with hydrochloric acid should be performed. Specifically, step (c) of precipitation with hydrochloric acid is preferably performed by centrifuging the enzymatically treated extract, adjusting the pH of the supernatant to a pH of 2.5 to 4.5, preferably 3.0 to 4.0, by addition of hydrochloric acid (HCl), and then precipitating the protein in the supernatant with hydrochloric acid in a refrigerator at 4° C. Particularly, the pH in the step of precipitation with hydrochloric acid is most preferably adjusted to 3.3-3.8 in order to maintain the activity and recovery rate of the toxin at high levels. If the step of precipitation with hydrochloric acid is carried out in the above-described pH range, the titer of the botulinum toxin will be as high as 90% or more, and the coagulation of protein will significantly decrease. Next, the precipitate with hydrochloric acid may be dissolved in buffer, and the subsequent step may be performed.

Step (d) that is the most important step is performed by chromatography using anion exchange resin after completion of the step of precipitation with hydrochloric acid in order to remove most major impurities other than the botulinum type A toxin. The anion exchange resin that is used in step (d) may be resin substituted with a diethylaminoethyl (DEAE) or quaternary ammonium (Q) group, but is not limited thereto. For example, the anion exchange resin may be DEAE-Sephadex as described in U.S. Pat. No. 5,696,077, International Patent Publication No. WO96/05222 and U.S. Pat. No. 5,846,929. Preferably, it is any one of anion exchange resins having a strongly basic quaternary ammonium group or weakly basic diethylaminoethyl (DEAE) group.

Examples of the strongly basic anion exchange group that can be used in the present invention may include Q Sepharose Fast Flow, Q Sepharose High Performance, Resource Q, Source 15Q, Source 30Q, Mono Q, Mini Q, Capto Q, Capto Q ImpRes, Q HyperCel, Q Cermic HyperD F, Nuvia Q, UNOsphere Q, Macro-Prep High Q, Macro-Prep 25 Q, Fractogel EMD TMAE(S), Fractogel EMD TMAE Hicap (M), Fractogel EMD TMAE (M), Eshmono Q, Toyopearl QAE-550C, Toyopearl SuperQ-650C, Toyopearl GigaCap Q-650M, Toyopearl Q-600C AR, Toyopearl SuperQ-650M, Toyopearl SuperQ-650S, TSKgel SuperQ-5PW (30), TSKgel SuperQ-5PW (20), or TSKgel SuperQ-5PW, but are not limited thereto and anion exchange resins known in the art may be used.

The column buffer that is used in step (d) may be sodium phosphate buffer or citrate buffer. Preferably, sodium phosphate buffer is used. The concentration of the column buffer is controlled to 30-70 mM, preferably about 40-60 mM. The pH of the column is controlled to about 3.5-7.5, and the flow rate of the mobile phase is controlled to 0.5-5.0 ml/min, preferably 1.0-3.0 ml/min. Further, the conductivity of the buffer is adjusted to 3-30 mS/cm, and the sample is injected after completion of the equilibration of the column. The toxin is eluted as flow-through, and most major impurities are adsorbed. Specifically, in step (d) of purification by anion exchange chromatography, the botulinum type A toxin is not adsorbed onto the anion exchange resin, and most major impurities are removed by adsorption.

In the present invention, the anion exchange chromatography in step (d) is preferably performed at a pH of 3.5-7.5, preferably 4.5-7.0, and a conductivity of 3-30 mS/cm, preferably 5-20 mS/cm.

In order to completely remove impurities remaining after anion exchange chromatography of step (d), the method for producing the botulinum toxin according to the present invention may, if necessary, further comprise the steps of: (e) treating the anion exchange chromatography fraction containing the botulinum toxin with ammonium sulfate ($(NH_4)_2SO_4$) to form a precipitate, and dissolving the precipitate in buffer; and (f) purifying the botulinum toxin by secondary anion exchange chromatography.

In step (e), the anion exchange chromatography fraction containing the botulinum toxin is treated with ammonium sulfate to form a precipitate, and the formed precipitate is dissolved in buffer. The step of precipitation with ammonium sulfate corresponds to a salting out process in which a salt (ammonium sulfate, etc.) that easily dissolves in water is added to a protein mixture to increase the ionic strength to thereby form a protein precipitate. If a desired protein precipitates mainly upon saturation with 30% (w/v) ammonium sulfate, the desired protein can be precipitated by precipitating out proteins other than the desired protein at a ammonium sulfate saturation concentration of 30% (w/v) or lower, and then adding ammonium sulfate to a saturation concentration of 30% (w/v) and can be collected by centrifugation. The salting out operation is frequently used as initial means. The ammonium sulfate solution that is used in step (e) may have an ammonium sulfate concentration of 10-50% (w/v), preferably 20-40% (w/v).

Next, in step (f), the botulinum toxin can be purified by anion exchange chromatography. Purification of the high-purity botulinum toxin according to the present invention is mostly performed by anion exchange chromatography (primary anion exchange chromatography) of step (d), and anion exchange chromatography (secondary anion exchange chromatography) in step (f) is performed in order to remove the remaining impurities and may be performed in the same manner as the anion exchange chromatography of step (d).

The resulting fraction containing the botulinum type A protein, obtained by the above-described purification method, may be sterilized and filtered to prepare a crude liquid. The prepared crude liquid may be frozen and stored until use.

Figure 2:
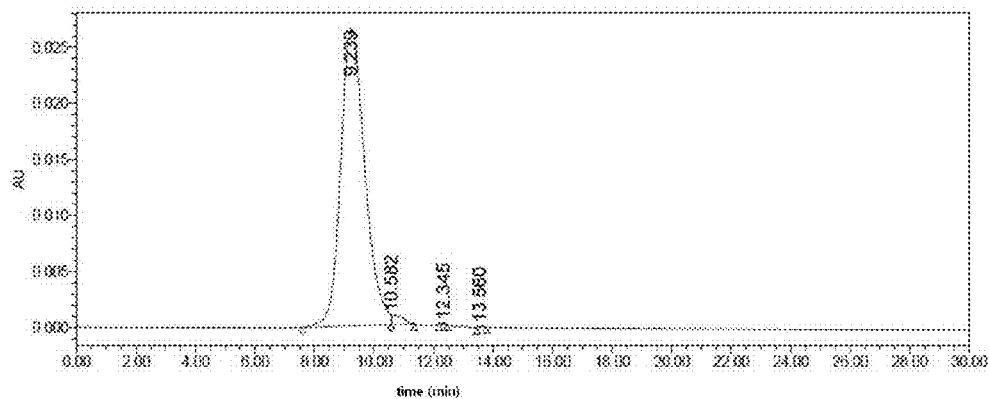
FIG. 2 shows the results of measuring the purity of a botulinum toxin after performing purification by primary anion exchange chromatography.
Figure 3:
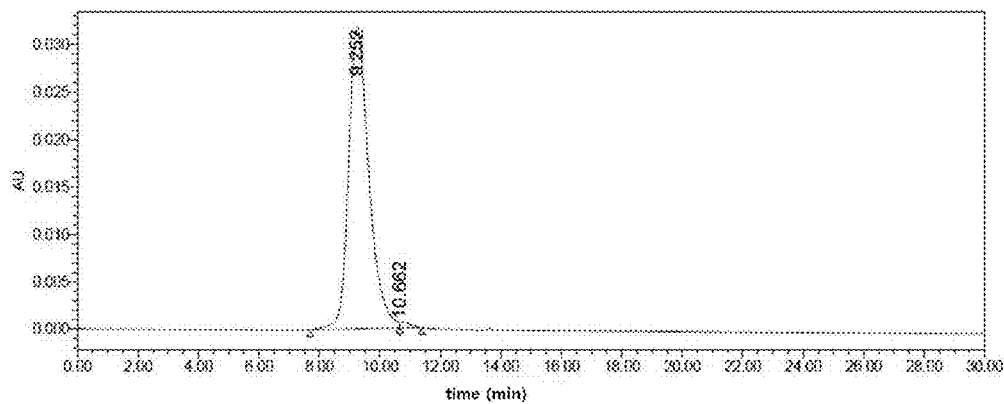
FIG. 3 shows the results of measuring the purity of a botulinum toxin after performing purification by secondary anion exchange chromatography.

In another aspect, the present invention is directed to a botulinum toxin produced by the method of the present invention. The purity of the botulinum toxin purified by HPLC was analyzed, and as a result, it could be seen that the purity of the botulinum toxin after primary anion exchange chromatography was 98.38% (FIG. 2), which is higher than the purity (about 95%) of BOTOX® commercially available from Allergan Inc., suggesting that most impurities were removed in the primary anion exchange chromatography step. Also, it was shown that the purity of the botulinum toxin after secondary anion exchange chromatography was 98.99% (FIG. 3).

Moreover, the method for production of the botulinum toxin according to the present invention has an advantage in that the steps of filtration, dialysis and ethanol precipitation can be omitted, and thus the process for production of the botulinum toxin is easy and simple. Particularly, the method of the present invention has an advantage in that the filtration and ethanol precipitation steps in the method for production of BOTOX® of Allergan Inc. (US Patent Publication No. 2012-0156756; Non-APF method) can be omitted, and thus the number of the purification steps can be reduced (from five steps to three steps) to reduce the period for production of a crude liquid of the botulinum toxin (from 4 weeks to 2 weeks).

In another example of the present invention, an experiment for comparison with the safety of BOTOX® (Allergan, Inc.) was performed in order to confirm the safety of the botulinum type A toxin protein (DWP450) produced by the method of the present invention. As a result, it was shown that the botulinum toxin (DWP450) produced by the method of the present invention showed a NOAEL value of 60 U/kg for females, suggesting that it is two times safer than BOTOX® (Allergan, Inc.) showing a NOAEL value of 30 U/kg. The two-times higher safety of the botulinum toxin produced by the method of the present invention is believed to be because the botulinum toxin of the present invention has high purity, and thus has an increased ability to act in a local area so that the systemic circulation of the botulinum toxin, which can result in side effects, is reduced.

The botulinum toxin produced by the method of the present invention is used as an active ingredient in a pharmaceutical composition. The botulinum toxin can be used for treatment of neuromuscular disorders characterized by hyperactive skeletal muscles. In addition, it can be used for various conditions, including a headache, a migraine headache, tension headache, a sinus headache, a cervicogenic headache, a sweating disorder, axillary hyperhidrosis, palmar hyperhidrosis, plantar hyperhidrosis, Frey's syndrome, hyperkinetic skin line, a facial wrinkle, glabellar lines, crow's feet, marionette lines, a nasolabial fold, a skin disorder, achalasia, strabismus, chronic anal fissure, blepharospasm, musculoskeletal pain, fibromyalgia, pancreatitis, tachycardia, prostatic enlargement, prostatitis, urinary retention, urinary incontinence, overactive bladder, hemifacial spasm, tremors, myoclonus, gastrointestinal disorders, diabetes, sialorrhea, detrusor-sphincter dyssynergia, post stroke spasticity, wound healing, juvenile cerebral palsy, smooth muscle spasm, restenosis, a focal dystonia, epilepsy, cervical dystonia, thyroid disorder, hypercalcemia, an obsessive compulsive disorder, arthritic pain, Raynaud's syndrome, striae distensae, peritoneal adhesion, vasospasms, rhinorrhea, muscle contracture, an injured muscle, laryngeal dystonia, writer's cramp and carpel tunnel syndrome.

As used herein, the term "pharmaceutical composition" means a formulation comprising the botulinum toxin as an active ingredient, and the formulation may comprise at least one additional ingredient (excipient) in the pharmaceutical composition in addition to the botulinum neurotoxin active ingredient. The additional ingredient may be selected from the group consisting of albumin, human serum albumin, recombinant human serum albumin, gelatin, sucrose, trehalose, hydroxyethyl starch, collagen, lactose, sucrose sodium chloride, polysaccharide, caprylate, polyvinylpyrrolidone and sodium, but is not limited thereto. Also, a method of preparing a pharmaceutical composition comprising the botulinum toxin as an active ingredient comprises a step of combining the botulinum toxin with an additional ingredient (excipient), and the combining step may be selected from the group of processes consisting of freeze drying, lyophilization and vacuum drying.

Therefore, a pharmaceutical composition is a formulation which is suitable for diagnostic, therapeutic or cosmetic administration (e.g. by intramuscular or subcutaneous injection or by insertion of a depot or implant) to a subject, such as a human patient. The pharmaceutical composition can be: in a lyophilized or vacuum dried condition, a solution formed after reconstitution of the lyophilized or vacuum dried pharmaceutical composition with saline or water, or; as a solution that does not require reconstitution. The active ingredient can be one of the botulinum toxin serotypes A, B, $C_1$, D, E, F or G or a botulinum toxin, all of which can be made natively by Clostridial bacteria. As stated, a pharmaceutical composition can be liquid or solid, for example vacuum-dried. Exemplary methods for formulating a botulinum toxin active ingredient pharmaceutical composition are disclosed in US Patent Publication No. 2003-0118598 published on Nov. 5, 2002.

In another example of the present invention, in order to confirm the effect of the botulinum type A toxin protein (DWP450) produced by the method of the present invention, the compound muscle action potential (CMAP) amplitude and the conduction velocities (tC) were measured. In the experiment, two different botulinum type A toxin proteins, BTX-A-1 (BOTOX®, Allergan Inc., California, USA) and BTX-A-2 (DWP450) produced by Example 2 of the present invention, were used in four divided groups. In group 1, 0.08 ml of sodium chloride (NaCl) was administered to one TA muscle, and another muscle was not treated. In group 2, 0.02 ml of BTX-A-1 (two units) was administered to one TA muscle, and 0.02 ml of BTX-A-2 (two units) was administered to another TA muscle. In group 3, 0.04 ml of BTX-A-1 (four units) was administered to one TA muscle, and 0.04 ml of BTX-A-2 (four units) was administered to another TA muscle. In group 4, 0.08 ml of BTX-A-1 (eight units) was administered to one TA muscle, and 0.08 ml of BTX-A-2 (eight units) was administered to another muscle.

One unit of botulinum toxin is defined as the $LD_{50}$ upon intraperitoneal injection into female Swiss Webster mice weighing about 18-20 grams each. One unit of botulinum toxin is the amount of botulinum toxin that kills 50% of a group of female Swiss Webster mice.

Figure 4:
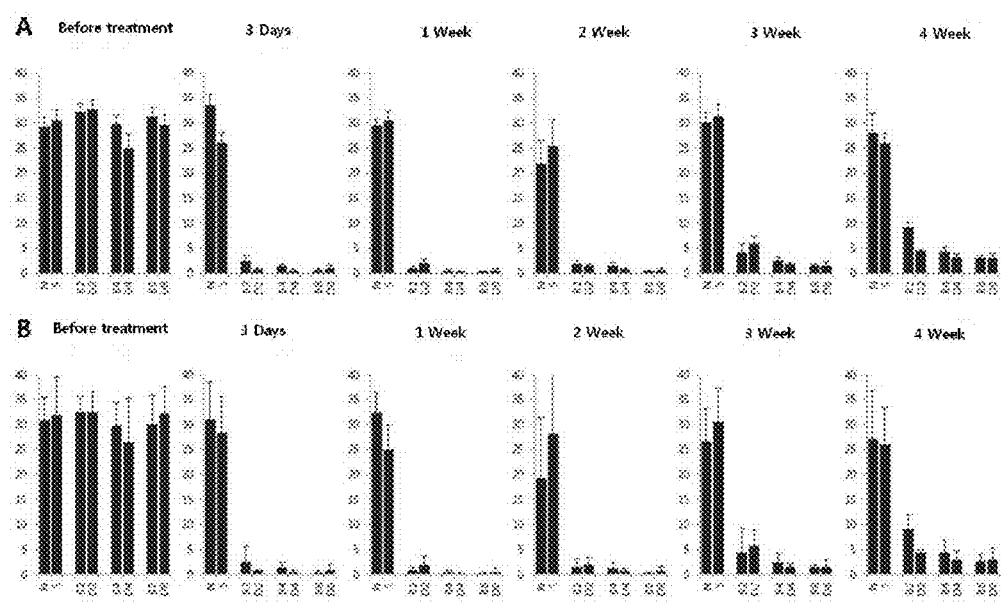
FIG. 4 shows the results of measuring the increase or decrease in compound muscle action potential amplitude caused by treatment with a botulinum toxin produced by the method of the present invention and BOTOX® (Allergan). N: no injection; S: saline injection; B2: BTX-A-1, two units; D2: BTX-A-2, two units; B4: BTX-A-1, four units; D4: BTX-A-2, four units; B8: BTX-A-1, eight units; and D8: BTX-A-2, eight units.

The compound muscle action potential (CMAP) amplitudes caused by administration of BTX-A-1 and BTX-A-2 were measured, and as a result, at a slow stimulus rate of 2 Hz, the groups administered with BTX-A-1 and BTX-A-2 showed a paralytic effect on the TA muscle (dY) at 3 days, 1 week, 2 weeks, 3 weeks and 4 weeks after administration (FIG. 4A), and at a fast stimulus rate of 20 Hz, the groups administered with BTX-A-1 and BTX-A-2 showed a paralytic effect on the TA muscle (dY) at 3 days, 1 week, 2 weeks, 3 weeks and 4 weeks after administration (FIG. 4B). There was no significant difference ($p<0.05$) between BTX-A-1 and BTX-A-2 at a slow stimulus rate of 2 Hz and a fast stimulus rater of 20 Hz, and the paralytic effect on the TA muscle (dY) in the groups administered with BTX-A-1 and BTX-A-2 was related to the dosage of botulinum toxin administered.

Figure 5:
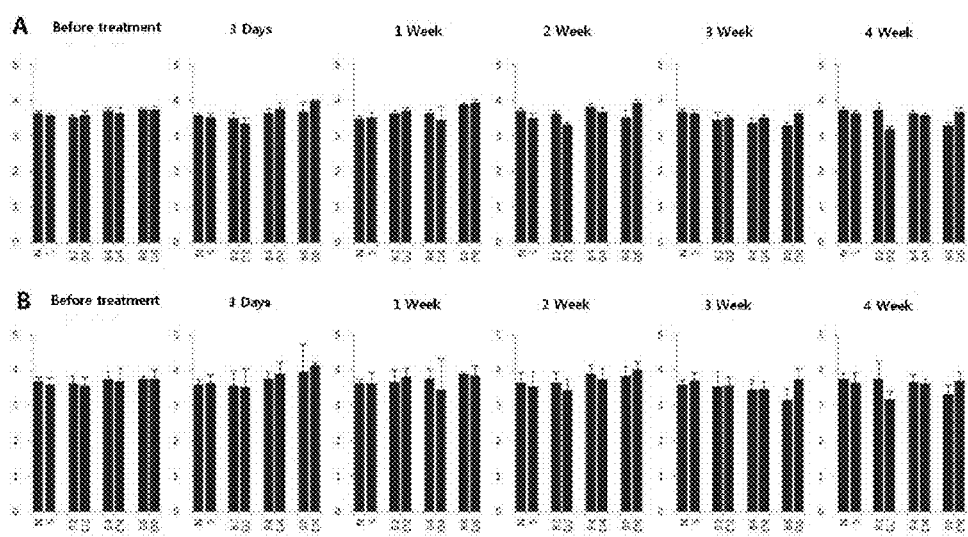
FIG. 5 shows the results of measuring conduction velocities caused by treatment with a botulinum toxin produced by the method of the present invention and BOTOX® (Allergan). N: no injection; S: saline injection; B2: BTX-A-1, two units; D2: BTX-A-2, two units; B4: BTX-A-1, four units; D4: BTX-A-2, four units; B8: BTX-A-1, eight units; and D8: BTX-A-2, eight units.

The conduction velocities (tC) caused by administration of BTX-A-1 and BTX-A-2 were measured, and as a result, it was shown that the groups administered with BTX-A-1 and BTX-A-2 did not induce a delay in conduction velocity at a slow stimulus rate of 2 Hz and a fast stimulus rate of 20 Hz (FIG. 5).

Specifically, the botulinum toxin produced by the method of the present invention exhibits an effect similar to that of commercially available BOTOX® (Allergan, Inc.) and is two times safer, because it has higher purity leading to a decrease in the systemic circulation property of the botulinum toxin. Thus, it can be used for various purposes, including treatment of neuromuscular disorders, removal of wrinkles, and treatment of spastic hemiplegia and cerebral palsy.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Culture of *Clostridium botulinum* Strain 1-1: Composition of Medium Used in Culture a medium having a composition comprising 2% casein hydrolysate, 1% yeast extract, 1% glucose and 0.5% thioglycollate was used for the seed culture and main culture of the *Clostridium botulinum* strain in order to produce a botulinum toxin.

1-2: Seed Culture of *Clostridium botulinum* Strain

20 µl of *Clostridium botulinum* (the Korean Centers for Disease Control and Prevention Accession No.: 4-029-CBB-IS-001) was inoculated into a culture tube containing 10 ml of a sterile medium having the composition described in Example 1-1 and was subjected to primary seed culture (stationary culture) at 35° C. for 22-30 hours under anaerobic conditions. When the growth of the strain in the primary seed culture was confirmed, 8 ml of the primary seed culture was inoculated into a 1 l culture bottle containing 800 ml of a sterile medium having the same medium composition and was subjected to secondary seed culture (stationary culture) at 35° C. for 8-15 hours under anaerobic conditions.

1-3: Main Culture of *Clostridium botulinum* Strain

In order to produce a botulinum toxin by culturing the *Clostridium botulinum* strain, the main culture of the strain was performed. Specifically, 9.3 l of a medium having the composition described in Example 1-1 was prepared and placed in a 10 l incubator, followed by sterilization of the medium. Nitrogen was supplied to make anaerobic conditions, and the growth of the strain was performed at a temperature of 35° C. and an agitation speed of 50 rpm.

The strain in the 1 l culture bottle subjected to secondary seed culture in Example 1-2 was inoculated into a 10 l incubator through an inoculation line connected to the inoculation port of the 10 l incubator. The *Clostridium botulinum* strain in the 10 l incubator was cultured under the conditions of 35° C. and 50 rpm and the set culture conditions were maintained, checked and recorded. When the strain was cultured for 100 hours or more, the main culture was completed.

Example 2

Production of Botulinum Toxin 2-1: Step of Precipitation with Sulfuric Acid

The step of precipitation with sulfuric acid is a protein separation process in which sulfuric acid is added to a culture containing many kinds of proteins to reduce the pH of the culture while killing botulinum bacteria remaining after culture so that the proteins reach the isoelectric point to precipitate. The main culture was performed as described in Example 1-3 and after completion of the main culture, 5N sulfuric acid was added to the culture by an automatic pump so as to reach a pH of 3.4-3.6 as measured by the pH sensor of the 10 l incubator, and then the culture was transferred to a 20 l container (AS ONE, Cat. No AS5.372.06) through the harvest line of the incubator, and the 20 l container containing the sulfuric acid precipitate was transferred to a biological safety cabinet (BSC). Then, precipitation with sulfuric acid was performed in the BSC.

2-2: Enzymatic Treatment and Toxin Extraction

After removal of the supernatant from the sulfuric acid precipitate, 700 ml of 1M sodium phosphate buffer (pH 5.3) was added to the precipitate. Then, the solution was adjusted to a pH of 5.0-6.0 by addition of 5N sodium hydroxide (NaOH). To remove DNA and RNA from the precipitate, 60 ml of 0.4M benzamidine HCl, 1 g of DNase and 1 g of RNase were added to and reacted with the solution for about 5 hours to extract the botulinum toxin.

2-3: Hydrochloric Acid Precipitation and Toxin Dissolution

The culture including toxin extract was centrifuged at 4° C. at 12000×g for 15 minutes to separate it into pellets and a supernatant, and the separated supernatant was transferred to a fresh 10 l bottle (AS ONE, Cat. No AS5.372.04), and then adjusted to a pH of 3.4-3.6 by addition of 1N hydrochloric acid (HCl) and subjected to hydrochloric acid precipitation in a refrigerator at 4° C. The hydrochloric acid precipitate was centrifuged at 4° C. at 12000×g for 15 minutes, and the supernatant was removed, after which 50 ml of sodium phosphate buffer (pH 6.5) was added to the toxin pellets to dissolve the toxin.

2-4: Primary Anion Exchange Chromatography

After completion of the precipitation process, in order to remove most major impurities other than the botulinum type A toxin, chromatography was performed using ion exchange resin. Specifically, anion exchange resin (Toyopearl SuperQ-650M, Tosoh Bioscience, P/N 17228) was packed into a column, after which the sample that precipitated in Example 2-3 was injected into the column, and the toxin was eluted with 50 mM of sodium phosphate elution buffer. In the primary purification step, the botulinum type A toxin protein was not adsorbed onto the anion exchange resin, and most major impurities were removed by adsorption. For purification of a high-purity botulinum toxin, the sample was maintained at a pH of 4.5-7.0 and a conductivity of 5-20 mS/cm.

2-5: Ammonium Sulfate Precipitation

Fractions containing the botulinum type A toxin protein purified by anion exchange chromatography were collected, and ammonium sulfate was added thereto at a concentration of 20-40% (w/v) to precipitate the botulinum type A toxin protein again. The precipitated botulinum type A toxin protein was dissolved again in 50 mM sodium phosphate (pH 6.5).

2-6: Secondary Anion Exchange Chromatography

After completion of the ammonium sulfate precipitation process, in order to remove minor impurities other than the botulinum type A toxin, chromatography using ion exchange resin was performed once more. Specifically, anion exchange resin (Toyopearl SuperQ-650M, Tosoh Bioscience, P/N 17228) was packed into a column, after which the ammonium sulfate precipitate dissolved in Example 2-5 was injected into the column, and the toxin was eluted with 50 mM sodium phosphate elution buffer. At this time, the botulinum type A toxin protein was not adsorbed, and minor impurities were removed by adsorption.

The purification of a high-purity botulinum toxin is mostly achieved in the primary anion exchange chromatography step, and the purification step by secondary anion exchange chromatography is performed in order to remove the remaining impurities. For purification of a high-purity botulinum toxin, the ammonium sulfate precipitate was maintained at a pH of 4.5-7.0 and a conductivity of 5-20 mS/cm.

2-7: Preparation of Crude Liquid

Fractions containing the botulinum type A toxin protein purified by anion exchange chromatography in Example 2-6 were collected, sterilized and filtered through a 0.2 μm filter to prepare a crude liquid. The prepared crude liquid was stored below −70° C. The produced botulinum type A toxin protein was named "DWP450".

Example 3

Analysis of Purity of Purified Botulinum Toxin

HPLC (e2695, Waters) was performed by SEC (size exclusion chromatography). The mobile phase used was 100 mM sodium phosphate buffer (pH 6.5), and a TSKgel G4000SW$_{XL}$ (Tosoh Bioscience, P/N 08542) column was connected to a guard column (Tosoh Bioscience, P/N 08543) for P/N 08542, and 20 μg of the botulinum type A toxin protein was loaded into the column and allowed to flow at a rate of 1 mL/min for 30 minutes. As a result, it was shown that the purity of the botulinum toxin after primary anion exchange chromatography was 98.38% (FIG. 2) and the purity of the botulinum toxin after secondary anion exchange chromatography was 98.99% (FIG. 3).

Example 4

Evaluation of Safety of Purified Botulinum Toxin

In order to confirm the safety of the botulinum type A toxin protein (DWP450) purified in Example 2, an experiment for comparison with the safety of BOTOX® (Allergan, Inc.) was performed.

SD (Sprague-Dawley) white male rats were divided into the following five groups, each consisting of 10 males and 10 females: a group administered with 30 U/kg of a test material (DWP450); a group administered with 60 U/kg of the test material; a group administered with 30 U/kg of a comparative material (BOTOX® available from Allergan, Inc.); a group administered with 60 U/kg of the comparative material; and a control group (saline). Each of the test material, the comparative material and saline was administered intramuscularly a total of five times a time a week for 5 weeks.

In the groups administered with 60 U/kg of the test material and 60 U/kg of the comparative material (BOTOX®), five females and five males were additionally added, and a comparative toxicity test was performed for a recovery period of 12 weeks in order to evaluate the reversibility of toxicity (Table 1).

TABLE 1

| | Evaluation of safety of purified botulinum toxin | | | |
|---|---|---|---|---|
| | | Dosage | NOAEL/MLD (Units/kg) | |
| Test | Species | (Units/kg) | DWP450 | Allergan |
| Comparative toxicity | SD rat | 0, 30, 60 | Male: <30 Female: 60 | Male: <30 Female: 30 |

As a result, it was shown that the botulinum toxin (DWP450) produced by the method of the present invention showed a NOAEL value of 60 U/kg for females, suggesting that it is two times safer than BOTOX® (Allergan, Inc.) showing a NOAEL value of 30 U/kg. The two-times higher safety of the botulinum toxin of the present invention is believed to be because the botulinum toxin of the present invention had high purity, and thus had an increased ability to act in a local site so that the systemic circulation of the botulinum toxin, which could result in side effects, was reduced.

Example 5

Examination of Effect of Purified Botulinum Toxin

In order to examine the effect of the botulinum type A toxin protein (DWP450) purified in Example 2, the compound muscle action potential (CMAP) amplitudes and the conduction velocities (tC) were measured.

Specifically, 24 SD (Sprague-Dawley) white rats were randomly divided into four groups, each consisting of six rats. Two different botulinum type A toxin proteins, BTX-A-1 (BOTOX®, Allergan Inc., California, USA) and BTX-A-2 (DWP450) purified in Example 2, were used. The two formulations had substantially identical characteristics as shown in Table 2 below, and the botulinum toxin diluted with 0.9% saline was used in all procedures. Rats were anesthetized by intraperitoneal injection of 10 mg/kg of ketamine hydrochloride, and then BTX-A-1 and BTX-A-2 were administered to the tibialis anterior (TA) muscle of the rats.

TABLE 2

Comparison of characteristics between BTX-A-1 and BTX-A-2

|  | BTX-A-1 (Allergan) | BTX-A-2 |
| --- | --- | --- |
| Clostridium botulinum strain | Wild-type hall | Wild-type hall |
| Serotype | Botulinum toxin type A | Botulinum toxin type A |
| Complex molecular weight (kDa) | 900 | 900 |
| Package (units/vial) | 100 | 100 |
| Excipients - Stabilizer | Human serum albumin | Human serum albumin |
| Excipients - Isotonic agent | sodium chloride | sodium chloride |
| Form | Vacuum dried | Lyophilized |
| Storage condition (° C.) | 2-8 | 2-8 |
| Shelf life (months) | 36 | 36 (ongoing) |
| pH | 6.0 ± 0.5 | 6.0 ± 0.5 |

In group 1, 0.08 ml of sodium chloride (NaCl) was administered to one TA muscle, and another TA muscle was not treated. In group 2, 0.02 ml of BTX-A-1 (two units) was administered to one TA muscle, and 0.02 ml of BTX-A-2 (two units) was administered to another TA muscle. In group 3, 0.04 ml of BTX-A-1 (four units) was administered to one TA muscle, and 0.04 ml of BTX-A-2 (four units) was administered to another TA muscle. In group 4, 0.08 ml of BTX-A-1 (eight units) was administered to one TA muscle, and 0.08 ml of BTX-A-2 (eight units) was administered to another muscle.

Level of delay in CMAPs and conduction velocities were measured using CyberAmp380 and Digidata1320 (Axon Instruments. Inc, USA). The electrodes used were attached to the skin using an alligator clip. The negative electrode was attached to the popliteal muscle, and the positive electrode was attached to the retropubic space and the greater trochanter of the femur. The recording electrode was attached to the belly muscle of the tibia anterior muscle, and the reference recording electrode was attached to the left hind calcaneal tendon and the sole.

An electric stimulation of 1-5 mA was applied at a slow stimulus rate of 2 Hz and a fast stimulus rate of 20 Hz. The paralytic effect on the TA muscle was determined by measuring the peak-to-peak amplitude of CMAPs (dY), and the delay in conduction velocity was determined by measuring the time gap between the stimulus point and negative peak point.

Analysis by the electric stimulation was performed before administration of BTX-A-1 and BTX-A-2 and at 3 days, 1 week, 2 weeks, 3 weeks and 4 weeks after administration, and the CMAPs and conduction velocities caused by administration of BTX-A-1 and BTX-A-2 were analyzed by ANOVA using SAS (Version 9.2, SAS Institute Inc., USA).

As a result, it was observed that, at a slow stimulus rate of 2 Hz, the groups administered with BTX-A-1 and BTX-A-2 showed a paralytic effect on the TA muscle (dY) at 3 days, week, 2 weeks, 3 weeks and 4 weeks after administration (FIG. 4A), and at a fast stimulus rate of 20 Hz, the groups administered with BTX-A-1 and BTX-A-2 showed a paralytic effect on the TA muscle (dY) at 3 days, 1 week, 2 weeks, 3 weeks and 4 weeks after administration (FIG. 4B).

There was no significant difference ($p<0.05$) between BTX-A-1 and BTX-A-2 at a slow stimulus rate of 2 Hz and a fast stimulus rater of 20 Hz, and the paralytic effect on the TA muscle (dY) in the groups administered with BTX-A-1 and BTX-A-2 was related to the dosage of botulinum toxin administered.

The conduction velocities (tC) caused by administration of BTX-A-1 and BTX-A-2 were measured, and as a result, it was shown that the groups administered with BTX-A-1 and BTX-A-2 did not induce a delay in conduction velocity at a slow stimulus rate of 2 Hz and a fast stimulus rate of 20 Hz.

Specifically, it was found that the botulinum toxin produced by the method of the present invention exhibited an effect similar to that of commercially available BOTOX® (Allergan, Inc.).

INDUSTRIAL APPLICABILITY

The use of the inventive method for production of a botulinum toxin makes it possible to produce a high-purity botulinum toxin by a simple process, suggesting that the inventive method is very economical and efficient. The botulinum toxin produced by the method of the present invention has high purity compared to botulinum toxins produced by conventional methods, and thus has an increased ability to act in a local area. Thus, the systemic circulation of the botulinum toxin, which can result in side effects, is reduced to increase the safety. Accordingly, the botulinum toxin of the present invention can be used for various purposes, including treatment of neuromuscular disorders, removal of wrinkles, and treatment of spastic hemiplegia and cerebral palsy.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for production of botulinum toxin, the method comprising the steps of:
   (a) treating a culture of a botulinum toxin-producing strain with acid to precipitate a botulinum toxin;
   (b) adding buffer to the precipitated botulinum toxin, followed by treatment with a protease inhibitor and nuclease, thereby extracting the botulinum toxin;
   (c) treating the extracted botulinum toxin with acid to precipitate the botulinum toxin and dissolving the precipitate in buffer; and
   (d) purifying the botulinum toxin by anion exchange chromatography,
   wherein the acid precipitation of step (c) is performed by adding sulfuric acid or hydrochloric acid to the extracted botulinum toxin, so that the extracted botulinum toxin reaches a pH of 2.5-4.5.

2. The method of claim 1, wherein the botulinum toxin-producing strain is *Clostridium botulinum*.

3. The method of claim 1, wherein the purified botulinum toxin is a botulinum type A toxin protein having a purity of at least 98%.

4. The method of claim 1, wherein the acid precipitation of step (a) is performed by adding sulfuric acid or hydrochloric acid, to the culture of the strain, so that the culture reaches a pH of 3.0-4.5.

5. The method of claim 1, wherein the protease inhibitor in step (b) is benzamidine HCl.

6. The method of claim 1, wherein the nuclease in step (b) is DNase and RNase.

7. The method of claim 1, wherein the extraction of the botulinum toxin in step (b) is performed at a pH of 4.5-6.5.

8. The method of claim 1, wherein the buffer in step (c) is sodium phosphate buffer.

9. The method of claim 1, wherein the anion exchange chromatography in step (d) is performed at a pH of 3.5-7.5, and a conductivity of 3-30 mS/cm.

10. The method of claim 1, further comprising, after step (d), the steps of:
    (e) treating the anion exchange chromatography fraction containing the botulinum toxin with ammonium sulfate to form a precipitate, and dissolving the precipitate in buffer; and
    (f) purifying the botulinum toxin by anion exchange chromatography.

11. The method of claim 10, wherein the ammonium sulfate in step (e) is added at a concentration of 10-50% (w/v).

12. The method of claim 10, wherein the buffer in step (e) is sodium phosphate buffer.

13. The method of claim 10, wherein the anion exchange chromatography in step (e) is performed at a pH of 3.5-7.5, and a conductivity of 3-30 mS/cm.

* * * * *